United States Patent [19]
Ruppert

[11] Patent Number: 6,129,691
[45] Date of Patent: Oct. 10, 2000

[54] PLIANT BACK SUPPORT APPARATUS WITH FOOT ENGAGEMENTS

[76] Inventor: John F. Ruppert, 32401 Botts Dr., Black Diamond, Wash. 98010

[21] Appl. No.: 09/275,913

[22] Filed: Mar. 24, 1999

[51] Int. Cl.[7] ..................................................... A61F 5/00
[52] U.S. Cl. .............................................. 602/19; 128/845
[58] Field of Search ......................... 602/5, 19; 128/845, 128/846, 869, 873, 874, 875, 876

[56] References Cited

U.S. PATENT DOCUMENTS

| | | |
|---|---|---|
| 406,663 | 7/1889 | McKinney . |
| 654,178 | 7/1900 | Mendenhall . |
| 903,403 | 11/1908 | Quick et al. . |
| 1,008,500 | 11/1911 | Thornton . |
| 1,202,851 | 10/1916 | Kelley ........................................... 2/93 |
| 1,409,326 | 3/1922 | Williamson .................................... 2/93 |
| 1,634,621 | 7/1927 | Martinez ........................................ 2/44 |
| 1,812,529 | 6/1931 | Haulbrook et al. ............................ 2/44 |
| 3,029,810 | 4/1962 | Martin ........................................ 128/78 |
| 3,295,517 | 1/1967 | Stevens ...................................... 128/78 |
| 3,570,011 | 3/1971 | Naig .............................................. 2/44 |
| 4,709,692 | 12/1987 | Kirschenberg et al. ................... 128/78 |
| 4,829,989 | 5/1989 | Deamer et al. ............................ 128/78 |
| 5,172,703 | 12/1992 | Tiede ........................................ 128/876 |
| 5,176,622 | 1/1993 | Anderson et al. .......................... 602/19 |
| 5,190,055 | 3/1993 | O'Connor ................................ 128/869 |
| 5,397,171 | 3/1995 | Leach ....................................... 128/875 |
| 5,548,843 | 8/1996 | Chase ......................................... 602/19 |
| 5,643,184 | 7/1997 | Toso ........................................... 602/19 |
| 5,647,827 | 7/1997 | Gutkowski et al. ...................... 482/124 |
| 5,709,648 | 1/1998 | Webb ......................................... 602/19 |
| 5,716,307 | 2/1998 | Vadher .................................... 482/125 |
| 5,816,251 | 10/1998 | Glisan ...................................... 128/845 |
| 5,860,944 | 1/1999 | Hoffman .................................... 602/19 |

*Primary Examiner*—Michael A. Brown
*Attorney, Agent, or Firm*—R. Reams Goodloe, Jr.

[57] ABSTRACT

A back support apparatus. The apparatus is fabricated with human dimensions including a torso harness (12) and two resilient leg strap assemblies (16) which terminate at and attach to a user's shoes. The harness (12) includes shoulder straps (22), a front strap (24), waistband clips (32), and a lumbar-supporting cincture (14). Positioned behind each leg of the user, the leg strap assemblies (16), include thigh straps (34), resilient members (20), ankle straps (40), sliding adjusters (42), and shoe clips (44). The waistband clips (32) attach to the user's waistband in front while the shoe clips (44) attach to the user's trailing shoe tops. The flexible torso harness (12) firmly embraces the user's upper body while the flexible leg strap assemblies (16) conform to the buttocks and legs. The lumbar-supporting cincture (14) braces the lower back of the user by its firm encirclement of the lumbar region but maintains flexibility with a multi-strap design vested in abdominal straps (28). Resilient members (20) stretch as the user bends over and consequently exert a downward pulling force on the rear side of the torso harness (12). This force results both in tightening the lumbar-supporting cincture (14), and in helping to lift the user in front.

20 Claims, 5 Drawing Sheets

PLIANT BACK SUPPORT APPARATUS WITH FOOT ENGAGEMENTS

This substitute specification incorporates the originally filed specification and the originally filed claims by this reference, as if fully set forth herein.

TECHNICAL FIELD

This invention relates to relief and prevention of back strain or injury in the human body, and more specifically to an apparatus which harnesses the torso and extends to the feet to effect such relief and prevention.

BACKGROUND

There are numerous devices available for back support. Many such devices may be classified as simple back braces, as they brace the back by partially immobilizing it with a network of straps and rigid elements. Since the user often needs flexibility of movement, such restrictive braces are not very useful.

Other devices, which are more complex than back braces, have metal springs or tubes to assist the user in returning to an upright position after bending over. These "stoop-labor" type devices are likewise inadequate since they are uncomfortable, cumbersome, and not suitable for extended use. Furthermore, they cannot be easily worn under clothing to minimize embarrassment.

A recent example of a stoop-labor type device is an invention shown in U.S. Pat. No. 5,709,648 issued to Webb on Jan. 20, 1998. It utilizes a vest having fiberglass rods located on the user's back to relieve strain from bending over. It falls short of being practical since it is bulky and does not allow the user to sit comfortably while wearing it.

Another recent example of a stoop-labor type device, shown in U.S. Pat. No. 5,860,944 issued to Hoffman on Jan. 19, 1999, employs metal springs to assist the user in restraightening. As in the above case, the Hoffman device is awkward, cannot be worn under clothing to minimize embarrassment, and cannot be used effectively in a sitting position.

OBJECTS AND ADVANTAGES

Accordingly, several objects and advantages of my back support apparatus are:
(a) to afford bracing for the user while standing;
(b) to deliver increased support to the user when bending over;
(c) to support the back while the user sits;
(d) to maintain body flexibility of the user;
(e) to provide comfort during extended use;
(f) to be adaptable to each user's size and strength needs;
(g) still further objects and advantages of my apparatus are that it is washable, is easy and inexpensive to make, is compact for shipping and storing, and it is able to be worn either partially or completely concealed under clothing to minimize embarrassment.

In sum, my back support apparatus is effective and highly practical. It provides the user with both a flexible back brace and with a responsive back support system which increases its supporting action as the user bends over. It delivers a high degree of injury prevention, as well as a healing action for preexisting back injuries.

Further objects and advantages of my back support apparatus will become apparent from consideration of the drawings and of the ensuing description.

BRIEF DESCRIPTION OF THE DRAWING

In the drawings, closely related figures have the same number but different alphabetic suffixes.

SUMMARY

My pliant back support apparatus comprises a network of fabric straps that encircle the torso of a person, springably extends behind the buttocks and legs to the feet, and engages the feet, to reduce or eliminate backache.

DESCRIPTION

Figure 1:
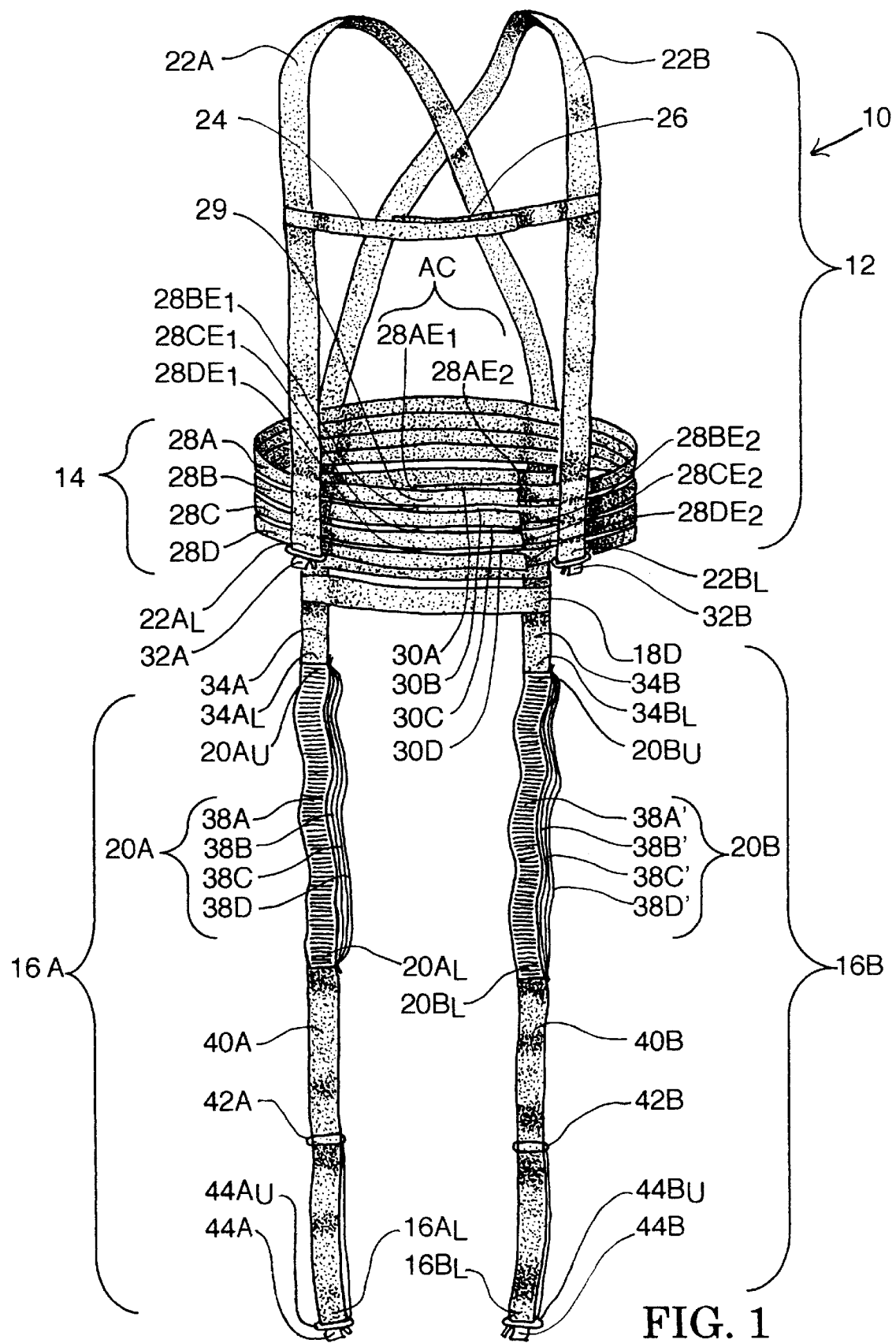
FIG. 1 is a front perspective view of my back support apparatus.
Figure 2:
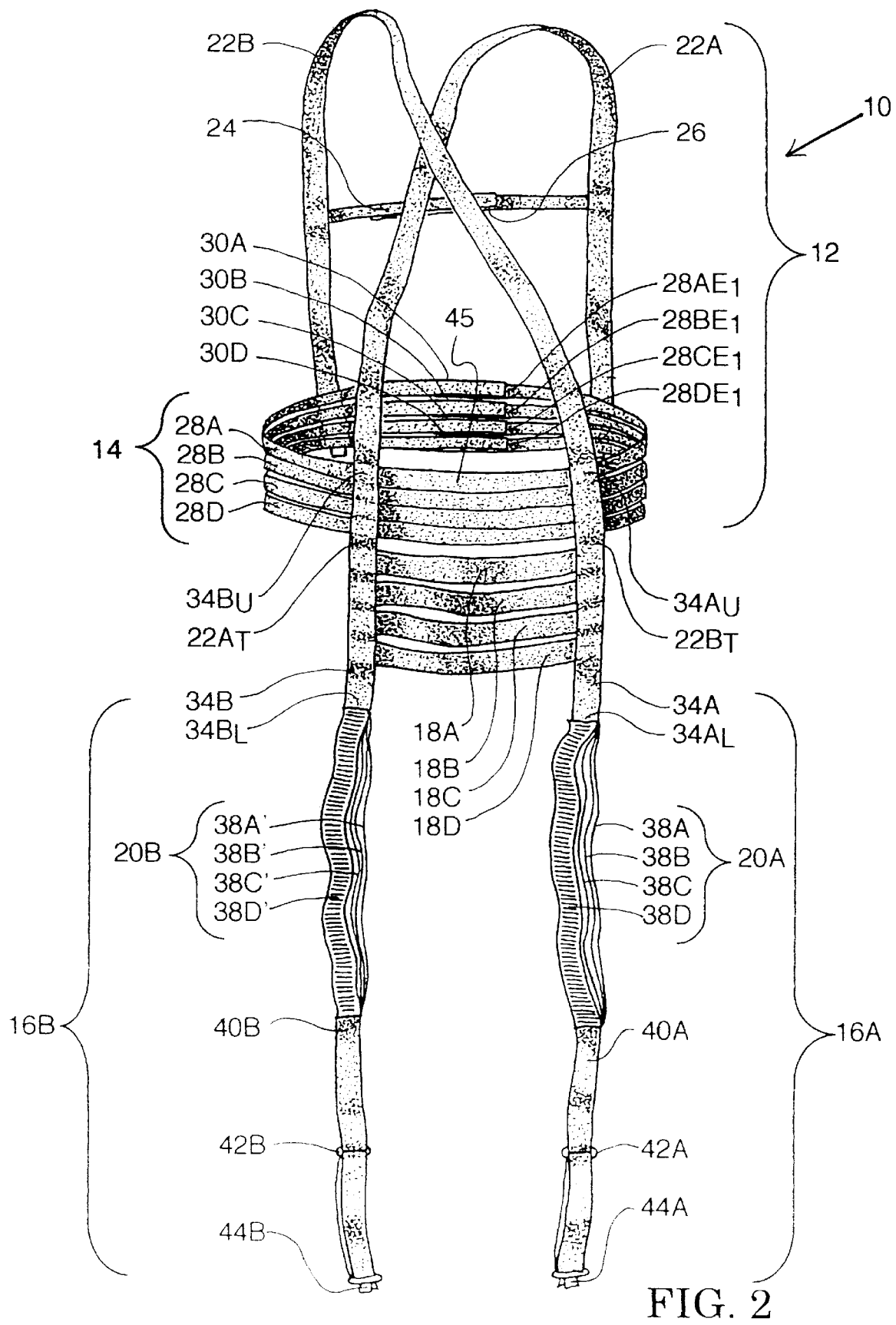
FIG. 2 is a rear perspective view of my back support apparatus.

The main embodiment of my back support apparatus 10 is illustrated in FIGS. 1 and 2. Back support apparatus 10 basically consists of a torso harness 12 (FIG. 1) as its upper half, leg strap assemblies 16A and 16B as its lower half, and interconnecting positioning elements 18A, 18B, 18C, and 18D (see FIG. 2) at mid position over the buttocks of the user U (see FIG. 5) to connect leg strap assemblies 16A and 16B.

FIG. 1 shows that harness 12 includes two shoulder straps 22A and 22B, a front strap 24, a lumbar-supporting cincture 14, and two waistband clips 32A and 32B. Shoulder straps 22A and 22B are crossed and connected to each other on the middle of the user's back (see FIG. 2) and individually connected to cincture 14 at their front or leading end portion 22A$_L$ and 22B$_L$ and at the back or trailing end portion 22A$_T$ and 22B$_T$ ends. Cincture 14 preferably includes four contiguous, parallel abdominal straps 28A, 28B, 28C, and 28D of about equal length. The ends 28AE$_1$, 28AE$_2$, 28BE$_1$, 28BE$_2$, 28CE$_1$, 28CE$_2$, 28DE$_1$ and 28DE$_2$ of each abdominal strap 28A, 28B, 28C, and 28D (see FIG. 1) have an overlapping area AC in front portion 29 of the cincture 14 which is positioned at the front of the user and joined with an adjustable closure such as a hook-and-loop fasteners 30A, 30B, 30C, and 30D, respectively. In other embodiments, cincture 14 could contain either less or more abdominal straps 28A, 28B, 28C, 28D, etc., depending on the size of the user U. A shorter than average person as user U may require three or less straps for best support, while a taller than average person as user U may need five abdominal straps. A single, wide belt of 5 cm (2 in) or more may also be employed in place of cincture 14. Shoulder straps 22A and 22B are coupled across the user's chest with front strap 24, which also employs a hook-and-loop fastener 26. In other embodiments, the front strap 24 may be omitted. Waistband clips 32A and 32B (see FIG. 1) complete harness 12 with their attachment to the leading ends of shoulder straps 22A and 22B immediately below cincture 14. Other embodiments may exclude waistband clips 32A and 32B.

In addition to the torso harness 12 discussed above, FIG. 2 shows that the back support apparatus 10 also includes two leg strap assemblies 16A and 16B. The leg strap assemblies 16A and 16B extend from the user's rear waistband, i.e, cincture 14, down to the user's ankles. Each leg strap assembly 16A or 16B includes a thigh strap 34A or 34B, respectively, a resilient member 20A or 20B, respectively, an ankle strap 40A or 40B, respectively, a sliding adjuster 42A or 42B, respectively, and a shoe clip 44A or 44B, respectively. Thigh straps 34A and 34B are each individually connected, preferably threadingly by sewing, with a predetermined spacing at their upper ends $34A_U$ and $34B_U$ to the rear portion 45 of cincture 14, by overlap of the thigh straps 34A and 34B with abdominal straps 28A, 28B, 28C, and 28D that comprise cincture 14. The lower ends $34A_L$ and $34B_L$ of thigh straps 34A and 34B connect to elastic members 20A or 20B which are positioned approximately behind the user's knees K (see FIG. 5) in this main embodiment. Each member 20A and 20B has four elastic straps, 38A, 38B, 38C, and 38D in the case of member 20A, and 38 A', 38B', 38C', and 38D' in the case of member 20B, in a layered configuration. Members 20A and 20B are connected at their upper end portion $20A_U$ and $20B_U$ to thigh straps 34A and 34B, respectively. Resilient members 20A and 20B are connected at their lower end portion $20A_L$ and $20B_L$ to to ankle straps 40A and 40B, respectively. Shoe clips 44A and 44B are attached to the terminal ends of ankle straps 40A and 40B, which employ sliding adjusters 42A and 42B approximately at their mid points. Shoe clips 44A and 44B are replaced with shoe loops 46A and 46B (see FIG. 3, or FIG. 4B) or foot loops 52A AND 52B (see FIG. 4C) in other embodiments.

As shown in FIG. 2, positioning elements 18 complete the main embodiment of apparatus 10. Each of the four positioning elements 18A, 18B, 18C and 18D connect orthogonally at opposite ends to thigh straps 34A and 34B, with a predetermined spacing width across the user U's buttocks, as earlier noted. Positioning elements 18A, 18B, 18C, and 18D could be replaced by a single pad or omitted, in other embodiments.

The basic construction details of the preferred and other embodiments of my device preferably include the following: All strap-on-strap connections are made by sewing, i.e, the connections are made using needle and thread, to provide a threadingly prepared connection, with the exception of hook-and-loop connections as discussed. The dominant strap material is preferably non-elastic cotton webbing. However, other strap materials such as nylon webbing could be substituted. Two strap sizes are preferably employed; (1) narrow webbing of about 2.5 cm (about 1 in) in width, and (2) wide webbing of about 5 cm (about 2 in) in width. Narrow webbing is used for front strap 24, and abdominal straps 28A, 28B, 28C and 28D. Shoulder straps 22A and 22B, thigh straps 34A and 34B, elements 18A, 18B, 18C, and 18D, and ankle straps 40A and 40B utilize wide webbing. Other strap sizes could be used such as narrower straps on back supports built for women or children. The all-important resilient members 20A and 20B are further defined as follows: Each member 20A and 20B, has a plurality of, and preferably four elastic straps 38A through 38D, and 38A' through 38D', respectively. Each elastic strap has a width of about 5 cm (2 in.) and a length of about 30 cm (12 in.), and is made of ribbed, elastic waistband, manufactured by Rhode Island Textile Company of Pawtucket, R.I. The specific number of elastic straps (four) used in each member 20A and 20B as illustrated in FIG. 1, for example, in the preferred embodiment will not be appropriate for every user. For each member 20A and 20B, four elastic straps is a nominal number for an adult male of average height of 1.78 m (5 ft, 10 in.) and weight of 79.4 kg (175 lbs.). Larger individuals may require a greater number of elastic straps 38A through 38D and 38A' through 38D', while smaller persons may need less straps. In addition to size, the work demands of the individual user U is another factor to consider when matching the characteristics of members 20A and 20B to the needs of the user U. A person involved in frequent, heavy lifting, or difficult, manual labor may require stronger resilient members 20A and 20B, and they therefore need to have a greater number of elastic straps than 38A through 38D and 38A' through 38D' included in their back support apparatus, i.e, a greater than the average number (four) of elastic straps behind each leg L of the user U. Waistband clips 32A and 32B and shoe clips 44A and 44B are preferably identical but are named differently simply to facilitate this discussion. Shoe clips 44A and 44B are attached at their upper end portion $44A_U$ and $44B_U$ to the lower end portion $16A_L$ and $16B_L$ of leg strap assemblies 16A and 16B. They are preferably industrial clips manufactured by the Albest Metal Stamping Company of Brooklyn, N.Y.

OPERATION

The operation of my back support apparatus 10 to protect the human back and to reduce back pain is many faceted. Experience has indicated that several beneficial mechanisms are operating simultaneously.

When the user U is not bent over (see FIG. 5), firmly-adjusted, lumbar-supporting cincture 14 gives the user back support by its reassuring compression of the abdominal region. Flexibility is maintained by a multi-strap design of lumbar-supporting cincture 14. The multi-strap design allows greater freedom of movement for the user than a single, wide belt would permit. Waistband clips 32A and 32B attach in front to the user's waistband W (see FIG. 5) to prevent unwanted upward shifting of cincture 14 during use.

When the user U bends over, more and greater forces are generated in apparatus 10 than in a standing-straight position. These forces derive from the angled lower back and are generated primarily in resilient members 20A and 20B, which become stretched as the user U bends over. They, in turn, exert a downward pull on the rear of torso harness 12 via thigh straps 34A and 34B, and thereby tend to lift the torso of the user U in front to assist in the user's restraightening.

Additionally, when the user U bends over, these newly generated forces give the user back support by another mechanism. This second mechanism involves a tightening effect on cincture 14. As the user bends over, the above mentioned forces in members 20A and 20B pull downward on the rear side of the cincture 14 and give rise to a tightening effect in the cincture 14 in its front and side areas (with respect to the user U) . This tightening effect pushes backward against the forward bend of the lumbar spine, supporting it, and in general, supporting the lower back of user U at its weakest point.

Although not vital to the operation of apparatus 10, positioning elements 18A, 18B, 18C and 18D help to insure that maximum tension is accumulated in resilient members 20A and 20B as the user bends over asymmetrically. Elements 18A through 18D, etc. hold thigh straps 34A and 34B (see FIG. 2) in a parallel relationship near the high region of the buttocks and cause maximum tension to be accumulated in members 20A and 20B. Maximum tension is desirable because it is this same tension which helps the user to return to an upright position. Maximum back support therefore results.

The initial tension of leg strap assemblies 16A and 16B is set by sliding adjusters 42A and 42B, which serve to adjust the lengths of ankle straps 40A and 40B. Adjusters 42A and 42B should be set so that the user U senses an unobjectionable, slight tug when walking but not set so tight that tension is felt while standing still.

Figure 3:
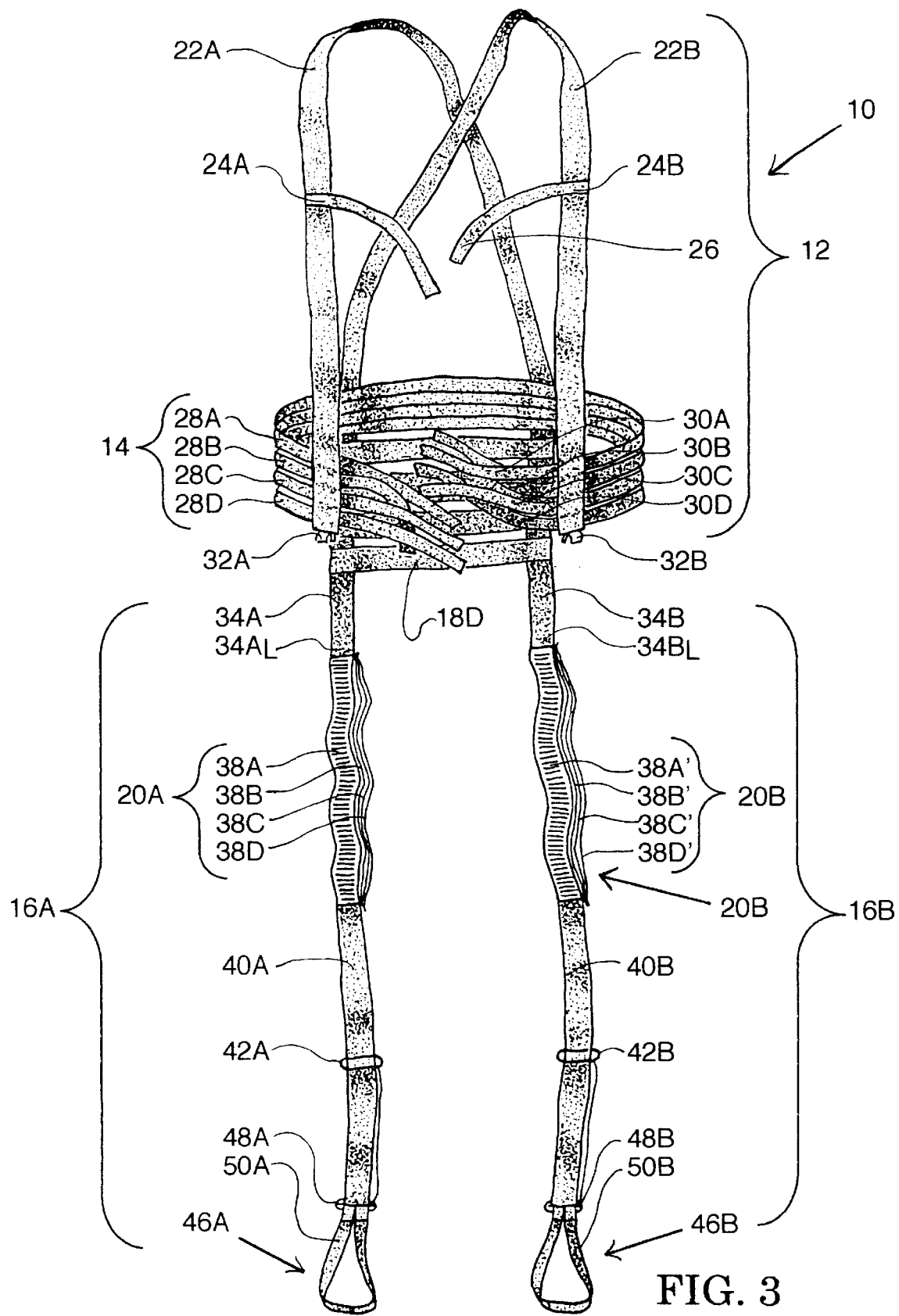
FIG. 3 is a front perspective view of my back support apparatus with loops for engaging the user's feet.

An alternative embodiment of my back support apparatus 10 is shown in FIG. 3. The foot engaging means or foot attachment device in this case are loops 46A and 46B. They differentiate this embodiment from the main embodiment shown in FIG. 1 (which uses shoe clips 44A and 44B as the preferred method of engaging the user's feet). FIGS. 4B and 4C illustrate in more detail the method of attaching fabric loops to engage the shoes S (FIG. 4B, shoe loops 46) and to engage the feet (FIG. 4C, foot loops 52) of the user. All hook-and-loop fasteners 30A, 30B, 30C, and 30D in FIG. 3 are shown in an opened configuration for further clarification.

Figure 4A:
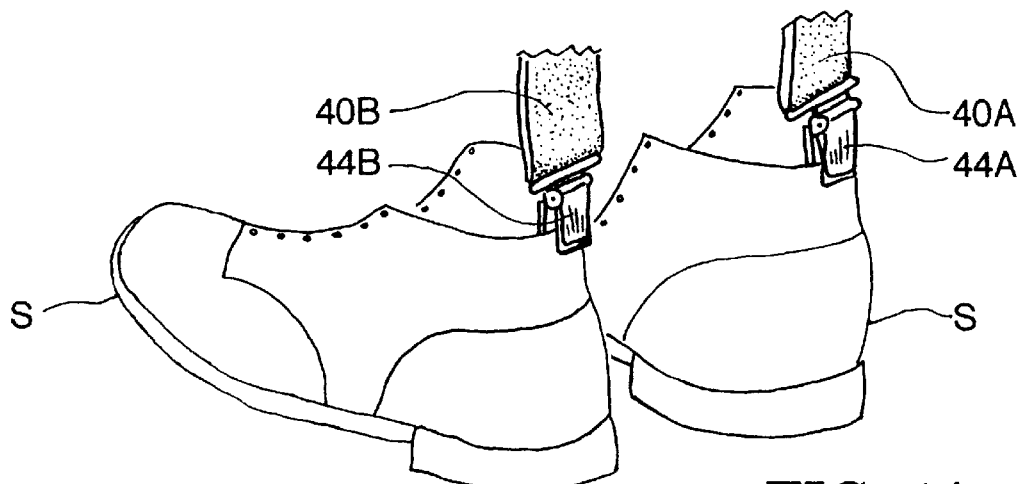
FIGS. 4A to 4C are rear perspective views of the devices and methods for engaging the user's feet.
Figure 4B:
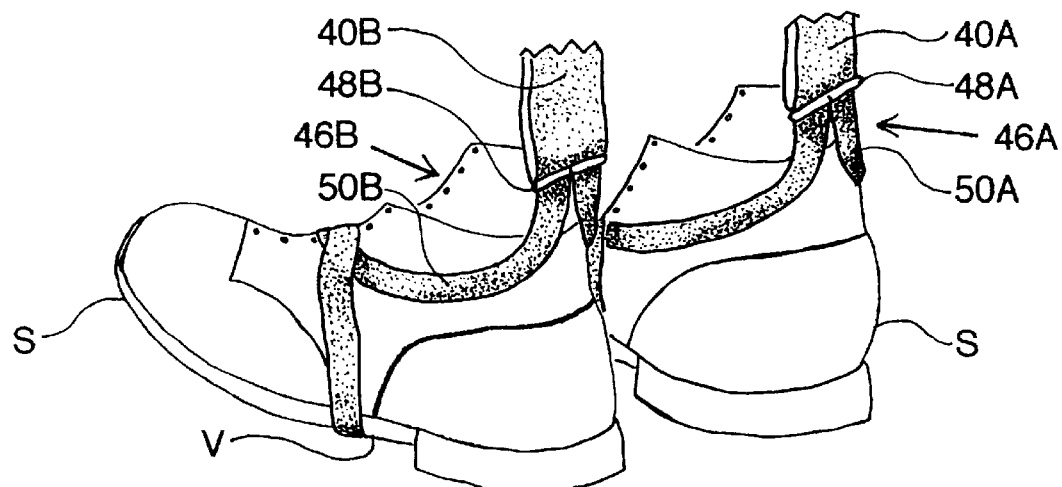
Figure 4C:
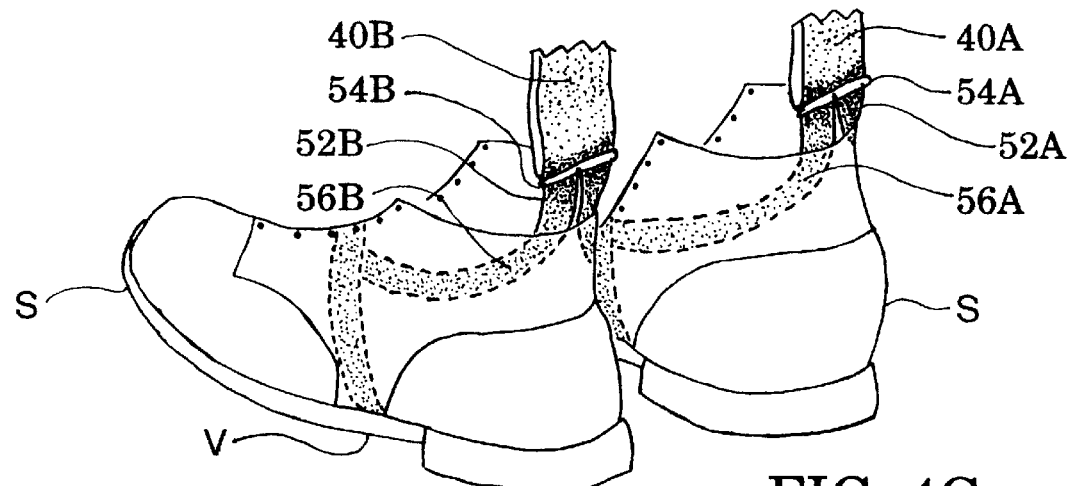

The various means for engaging and attaching the leg strap assemblies 16A and 16B to the user's feet are shown in FIGS. 4A to 4C. FIG. 4A shows the preferred manner in which shoe clips 44A and 44B are attached to the user's shoes. FIG. 4B shows the preferred manner in which shoe loops 46A and 46B are attached to the user's shoe S by wrapping once around the middle of the shoe or "vamp" V with the "D" ring, namely 48A or 48B, positioned to the rear of the shoe S. Alternatively, FIG. 4C shows the manner in which foot loops 52A and 52B can be used inside the user's shoe by encircling the instep of the foot, with the "D" ring 54A or 54B again positioned in back.

Figure 5:
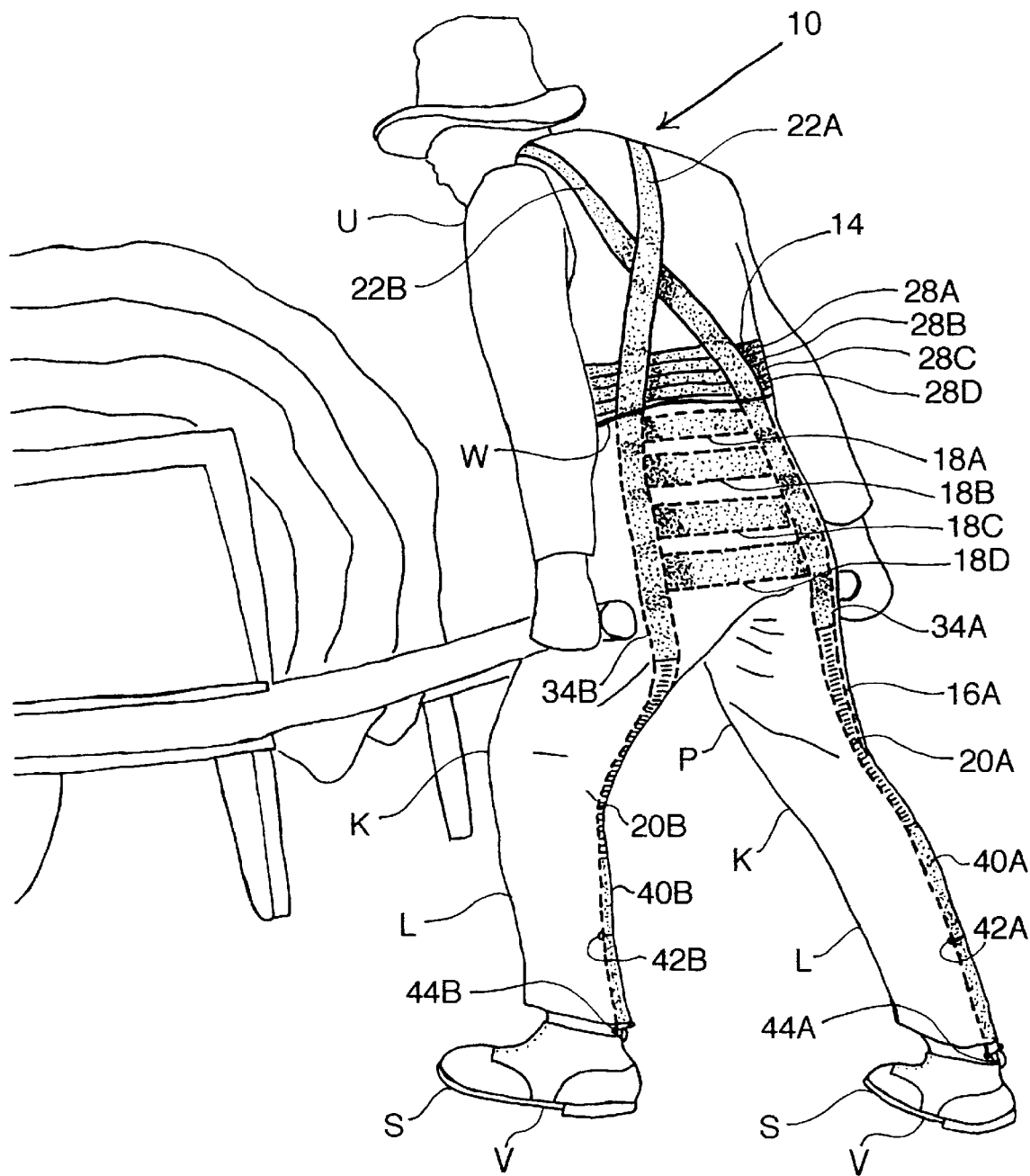
FIG. 5 is a rear perspective view of a worker wearing my back support apparatus.

A worker is shown wearing the main embodiment of my back support apparatus 10 in FIG. 5. The lower half of the apparatus 10 is worn under the work pants P and is thus shown in broken lines in this FIG. 5, and is attached to the shoes S by shoe clips 44A and 44B. The shoe clip 44A and 44B attachments are shown more clearly in FIG. 4A. Waistband clips 32A and 32B are presumably in use on the worker's front waistband but are not visible in this rear perspective view in FIG. 5.

Accordingly, my back support apparatus is highly compatible with the human form. It is easily put on or taken off. It is soft, lightweight, flexible, and hand washable. The cotton fabric and open-space design assist in cooling the worker. My apparatus can be worn for long periods of time without undue discomfort and can be used in virtually all work positions including standing, sitting, or kneeling. The user can wear it entirely concealed under ordinary clothing to eliminate embarrassment in public. My apparatus is easy to build from inexpensive materials and easy to repair. People of all sizes can be appropriately fitted by simply altering the sizes and/or numbers of straps used in assembly. The weight and work requirements of each user can be accommodated by selecting the appropriate number of elastic straps in resilient members 20A and 20B. My apparatus will enable a person with a weak or damaged back to confidently return to work and other normal activities.

It is an important benefit of my back support apparatus 10 that it responds positively to the work demands of the user. As the user increasingly bends over, it responds with greater support through increased loading of resilient members 20A and 20B. Additionally, the more weight the worker lifts, the more the stomach muscles expand against firm lumbar-supporting cincture 14, which in turn gives increased bracing and support. The user at rest has only a minimal awareness of apparatus 10. It will fulfill an immense need for an effective, user-friendly back support apparatus.

Although my above description contains many specificities, these should not be construed as limitations on the scope of my back support apparatus, but rather as an exemplification of one preferred embodiment thereof. Many other variations are possible as follows: The number of straps in lumbar-supporting cincture 14 could be reduced from four abdominal straps 28A, 28B, 28C, and 28D, shown in FIG. 1, to perhaps three straps for a user who is shorter than an average adult or increased to five straps for a taller than average user. Minimally, a single, wide belt may be used in place of multi-strap cincture 14, and it could be made of elastic material rather than the preferred non-elastic cotton webbing. Hook-and-loop fasteners are not an absolute requirement to secure the straps. Buckles, snaps, or other connectors may suffice. Waistband clips 32A and 32B could be replaced with other attaching devices or done away with altogether, however, to the detriment of apparatus 10 since clips 32A and 32B prevent unwanted upward movement of lumbar-supporting cincture 14. The combination of shoulder straps 22 and front strap 24 could conceivably be replaced by a vest of some sort. Additionally, metal springs could replace resilient members 20A and 20B, or roll-up springs could be attached to the user's shoes. Shoe clips 44A and 44B could be replaced by shoe loops or foot loops as indicated in the preceding discussion. Positioning elements 18A, 18B, 18C, and 18D may be changed in number and/or size including replacement by a single piece of fabric. The basic material of construction, cotton webbing, could easily be substituted with nylon webbing or other appropriate material. Dimensions may reasonably be altered without changing the basic operation or concept of the apparatus.

My back support apparatus will provide a wide range of individuals with an economical means of reducing back pain from past injuries and of preventing future injuries. Those persons performing strenuous labor, as well those involved in more sedentary occupations, will benefit greatly. Retirees who have chronic back problems will discover than my apparatus can help them live more comfortably and more productively. In addition, with minimal changes, my apparatus may help pregnant women cope with the extra weight associated with pregnancy.

Thus, the scope of my back support apparatus should not be determined by the embodiments illustrated, but by the appended claims and their legal equivalents.

What is claimed is:

1. A back support apparatus, said apparatus for support of a human user having (i) a chest, (ii) waist region, (iii) an abdomen, (iv) a back with shoulders, a middle, and a lumbar region having a preselected height, (v) buttocks, (vi) legs, (vii) and feet, said apparatus comprising:

(a) a lumbar-supporting cincture, said cincture adapted to firmly encompass said user's waist in the lumbar region, said cincture sized to substantially span said height of said lumbar region, wherein said cincture further comprises (i) a front portion, (ii) a rear portion having an upper portion, and (iii) an adjustable closure, (b) a pair of shoulder straps, said shoulder straps each comprising a leading end portion, and a trailing end portion, each shoulder strap sized to accommodate said user's shoulders, said shoulder straps individually joined in a predetermined spaced apart relationship at their leading end portions to said cincture at its front portion, said shoulder straps being individually joined at their trailing end portions to said cincture at its upper rear portion, with a predetermined spacing between said shoulder straps, (c) a pair of resilient leg strap assemblies, each of said pair of resilient leg strap assemblies comprising an upper end portion, and a lower end portion, each of said resilient leg strap assemblies disposed behind said user's buttocks and legs, wherein each of said pair of leg strap assemblies are individually joined with a predetermined spacing at their upper end portions to said cincture on the rear portion thereof, and each of said resilient leg strap assemblies having sufficient length to span between said cincture and said feet of said user, and (d) a pair of foot attachments, each of said foot attachments adapted for coupling of said resilient leg strap assemblies to said feet of said user, whereby said pair of resilient leg strap assemblies elongate as said user bends over and accumulate tension, and consequently, in combination with said shoulder straps, said cincture, and said pair of foot attachments, aid said user in restraightening.

2. The back support apparatus as set forth in claim 1 wherein said shoulder straps cross over each other, and connect to each other at said crossover, said crossover proximate said middle of said user's back.

3. The back support apparatus as set forth in claim 1 further comprising a front strap, said front strap comprising:

(a) a pair of fabric straps of predetermined size, each one of said pair of fabric straps comprising a free end, and each joined at only one end directly opposite one another, to one of said pair of said shoulder straps at said chest of said user, said pair of fabric straps each oriented substantially at right angles to said shoulder straps, said pair of fabric straps aligned to overlap with each other at their free ends, and (b) an adjustable closure for reversibly attaching said free ends of said pair of fabric straps each to the other, whereby said front strap maintains said shoulder straps at a predetermined distance from one another as said user bends over or twists.

4. The back support apparatus as set forth in claim 3 wherein said adjustable closure is a hook-and-loop fastener.

5. The back support apparatus as set forth in claim 1, further comprising a pair of suspender clips of a predetermined size, said suspender clips each attached to one of said leading end portions of said pair of shoulder straps, and disposed immediately beneath said front portion of said lumbar-supporting cincture, wherein said pair of suspender clips are adapted for attachment to a waistband of said user during use of said apparatus, and whereby said suspender clips prevent said cincture from displacing upward on the abdomen of said user during bending movements.

6. The back support apparatus as set forth in claim 1 wherein said lumbar-supporting cincture comprises a plurality of parallel abdominal straps, each one of said plurality of parallel abdominal straps having an adjustable closure.

7. The back support apparatus as set forth in claim 6 wherein said adjustable closure comprises a hook-and-loop fastener connected to said abdominal strap for reversibly closing said abdominal straps at said abdomen of said user.

8. The back support apparatus as set forth in claim 6 wherein said plurality of abdominal straps comprises four said abdominal straps.

9. The back support apparatus as set forth in claim 1 wherein said pair of foot attachments comprise a pair of shoe connectors, each of said shoe connectors adapted for coupling said leg strap assemblies to shoes worn by said user.

10. The back support apparatus as set forth in claim 9 wherein said pair of shoe connectors comprise a pair of shoe clips of a preselected size, each of said shoe clips having an upper end portion, and wherein said shoe clips are attached at their upper end portions to the lower end portions of said leg strap assemblies, wherein said shoe clips are reversibly attached to said user's shoes during use of said support apparatus, whereby said shoe clips anchor the lower extremities of said apparatus to the user's shoes.

11. The back support apparatus as set forth in claim 9 wherein said pair of shoe connectors comprise a pair of shoe loops, said shoe loops adapted for reversibly attaching said leg strap assemblies to the shoes of said user, said shoe loops each comprising:

(a) a D-ring of predetermined size, and (b) a strap of sufficient length to wrap once around a shoe of said user at its vamp, said strap having two ends each individually connected to the same D-ring, and said D-ring to the lower end portion of said leg strap assemblies, wherein said shoe loops are looped around said user's shoes to anchor said apparatus to the user's shoes.

12. The back support apparatus as set forth in claim 1 wherein each of said pair of leg strap assemblies comprise:

(a) a thigh strap, said thigh strap comprising an upper end portion, said upper end portion individually joined to said lumbar-supporting cincture on the rear portion thereof, (b) a resilient member substantially disposed behind said user's thighs and knees, said resilient member joined at its upper end portion to said thigh strap at the lower end portion thereof, and (c) an ankle strap for connecting the lower end portion of said resilient member to the upper end portion respectively of said foot attachment, whereby said resilient member elongates as said user bends over, accumulates tension, and subsequently supplies the pulling forces which aids said user in restraightening.

13. The back support apparatus as set forth in claim 12 wherein said resilient members each comprise a plurality of elastic straps, each of said plurality of elastic straps comprising upper and lower end portions, said plurality of elastic straps connected to each other solely at their respective upper and lower end portions, said elastic straps provided in a layered configuration.

14. The back support apparatus as set forth claim 13 wherein said plurality of elastic straps comprises four said elastic straps for each said resilient member.

15. The back support apparatus as set forth in claim 12 wherein said pair of ankle straps each include a sliding adjuster of a predetermined size, said sliding adjuster disposed substantially at the mid portion of said ankle strap, said sliding adjuster in combination with said ankle strap, provides a means for setting an initial tension load on said resilient member while said user is standing straight.

16. The back support apparatus as set forth in claim 12, further comprising one or more positioning elements, said one or more positioning elements joined on opposing end portions to each of said thigh straps, whereby said one or more positioning elements maintain said thigh straps in a parallel relationship at said buttocks of said user when said user bends over.

17. The back support apparatus as set forth in claim 16 wherein said one or more positioning elements comprise a plurality of positioning elements.

18. The back support apparatus as set forth in claim 17 wherein said plurality of positioning elements comprise four straps.

19. The back support apparatus as set forth in claim 18 wherein each of said positioning elements are made of pliant, non-resilient, cotton webbing.

20. A method for supporting the lower back of human user having (i) a chest, (ii) waist region, (iii) an abdomen, (iv) a back with shoulders, a middle, and a lumbar region having a preselected height, (v) buttocks, (vi) legs, (vii) and feet, said method comprising the steps of:

(a) securing a lumbar-supporting cincture around the waist of the user for firmly encompassing the user's waist in the lumbar region, said cincture being sized to substantially span the height of the lumbar region, (b) attaching a pair of shoulder straps to said cincture, wherein said shoulder straps are of appropriate size to accommodate the user's shoulders and are individually joined by overlap on their leading end portions to said cincture on its front portion with a predetermined spacing between each of said shoulder straps, said shoulder straps are individually joined on their trailing end portions to said cincture on its upper rear portion with a predetermined spacing between said shoulder, straps, and wherein said pair of shoulder straps are joined to said cincture at substantially right angles to said cincture and are non resilient, (c) engaging the shoulders of the user with said pair of shoulder straps respectively, (d) attaching a pair of resilient leg strap assemblies to said lumbar-supporting cincture, wherein said assemblies are disposed behind the user's buttocks and legs and are individually joined with a predetermined spacing on their upper end portions to said cincture on the rear portion thereof and are joined to said cincture at substantially right angles to said cincture, and wherein said assemblies each have sufficient length to span the distance between said cincture and the feet of the user and terminate near the feet with a free end, (e) attaching a pair of foot engaging means to said free ends of said leg strap assemblies respectively, and (f) engaging said pair of foot attachments with the feet of the user, whereby said leg strap assemblies, elongate as the user bends over, accumulate tension, and consequently, in combination with said shoulder straps, said cincture, and said pair of foot attachments, aid the user in restraightening.

\* \* \* \* \*